United States Patent [19]

Gervasutti et al.

[11] Patent Number: 4,754,085

[45] Date of Patent: Jun. 28, 1988

[54] PROCESS FOR THE PREPARATION OF HYDROFLUOROALKANES

[75] Inventors: Claudio Gervasutti, Venice; Lino Conte; Gian Paolo Gambaretto, both of Padua, all of Italy

[73] Assignee: Ausimont S.p.A., Milan, Italy

[21] Appl. No.: 920,595

[22] Filed: Oct. 20, 1986

[30] Foreign Application Priority Data

Oct. 21, 1985 [IT] Italy .................................. 22564 A/85

[51] Int. Cl.⁴ ..................... C07C 17/04; C07C 17/02; C07C 19/02; C07C 19/045
[52] U.S. Cl. .................................. 570/175; 568/683; 568/684; 570/134; 570/137
[58] Field of Search ........................ 570/175, 134, 137; 568/683, 684

[56] References Cited

U.S. PATENT DOCUMENTS

| | | | |
|---|---|---|---|
| 2,013,030 | 9/1935 | Calcott et al. | 570/175 |
| 2,716,141 | 8/1955 | Meller | 570/155 |
| 3,917,726 | 11/1975 | Von Halasz | 570/175 |
| 3,962,358 | 6/1976 | Von Halasz | 570/134 |

FOREIGN PATENT DOCUMENTS 77114 4/1983 European Pat. Off. ............ 568/683

Primary Examiner—J. E. Evans
Attorney, Agent, or Firm—Patricia Q. Peake

[57] ABSTRACT

Process for the preparation of hydro(halo)fluoroalkanes by direct fluorination in liquid phase with elemental fluorine at low temperature (under 0° C.) of the corresponding hydro(halo)=alkenes.

4 Claims, No Drawings

PROCESS FOR THE PREPARATION OF HYDROFLUOROALKANES

BACKGROUND OF THE INVENTION

1. Field of the invention

The present invention relates to a process for the preparation of hydro(halo)fluoroalkanes by starting from the respective hydro(halo)alkenes.

2. The Prior Art.

Hydrofluoroalkanes can be obtained by reduction with LiAlH4 [Ber. 97(7) 1964], or by U.V. irradiation of halofluoroalkanes in the presence of an alcohol (Czech 136,735). However, none of this processes can be applied in industial operations; because of the high cost of the reactants, or due to the difficulties relating to the equipment required for similar treatments in case of LiAlH$_4$; or due to the use of U.V. light. Moreover, the process of reduction by U.V. is limited, in that by it only a few specific mono- or dihydrogenated on the same carbon atom can be obtained.

In fact, by the said process, the introduction in the molecule of the first hydrogen atom can result relatively simple, even if the reaction times can even be of the order of twenty hours, but the introduction in the molecule of the second hydrogen atom is more difficult than that of the first one, and however no compounds di-hydrogenated on adjacent carbon atoms are obtained.

Also such fluorination processes are known, as the electrofluorination, carried out on hydrocarbons (J. Electrochem. Soc. 95, 47, 1949), but such a process results burdensome as regards the equipment and from the energetic viewpoint; and, above all, side reactions of fragmentation occur. Known are also fluorinations of hydrocarbons carried out with elemental fluorine, generally diluted with nitrogen, in the gaseous phase over Cu/Ag catalyst [Ind. Eng. Chem. 39, 290 (1947)]. However, also such processes are heavily limited in that they lead to the formation of side reaction by-products, such as high amounts of fragmentation products, or dimers and trimers.

Fluorinating halogenated olefins with CoF$_3$ is known as well [J. Org. Chem. 28, 494 (1963)], but side reactions occur, such as intramolecular H/fluorine, halogen/fluorine substitutions.

Thus, by this process, selectively preparing alkanes from olefins is not possible.

Furthermore, such a fluorination process requires particularly sophisticated equipment withstanding the fluorine used to regenerate CoF$_3$ (Temperature around 300° C.).

THE PRESENT INVENTION

The need thus existed of producing, by a process easily accomplishable on an industrial scale, saturated compounds belonging to the class of hydro(halo)-fluoroalkanes, both monohydrogenated and containing H atoms on adjacent C atoms.

It was necessary as well to have available a fluorination process, by which the by-products dimers, trimers, and addition polymers could be kept to a minimum, at the same time the contemporaneous substitution by fluorine of the hydrogen or halogen atoms of the starting product being kept within very low percent values.

It has been surprisingly found now that by carrying out the fluorination reaction on hydro(halo)olefins with elemental fluorine at low temperature, under 0° C., the reaction of fluorine addition to the double bond is preferred to the reaction of substitution of the hydrogen atoms and/or of the halogen atoms different from fluorine contained in the olefin, the substitution products being contained in very low percentages. The formation of the addition dimer products results moreover very low, whilst not even traces of the trimers or the polymers are formed.

The object of the present invention is hence a process for the fluorination in the liquid phase with elemental fluorine at a temperature lower than 0° C. of hydrohaloalkenes or of hydroalkenes having the following general formulae:

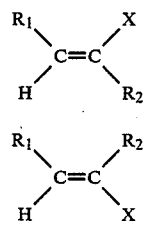

wherein:

X=H, F, Cl, Br

R$_1$, R$_2$=H, F, Cl, Br, C$_1$-C$_3$-alkyl or alkoxy, wherein the H atoms can also be completely substituted by such halogens as Cl, F.

The fluorination process according to the present invantion is carried out in the liquid phase at temperatures comprised within the range of from 0° C. to −100° C., preferably of from −70° C. to −85° C., the liquid phase being constituted by the same reactant and by the reaction products. Also solvents present in an amount comprised within the range of from 1 to 20 parts, preferably of from 4 to 10 parts by weight (w/w) per each part of hydro(halo)olefin, can be used. Useable solvents are completely fluorinated alkanes, liquid at the temperatures the reaction is carried out at, inert under the fluorination conditions. Preferred solvents are CFCl$_3$, CF$_2$Cl$_2$ and CF$_2$Cl-CF$_2$Cl.

The elemental fluorine is preferably used diluted with inert gases, such as nitrogen, in inert gas/F2 molar ratios comprised within the range of from 5 to 15.

The reaction can be carried out under the atmospheric, or under a lower pressure.

The process of the present invention allows the desired product to be obtained with a high selectivity, at the same time a high conversion of the starting product being obtained.

A further advantage of the process of the invention is that the fluorination of olefins by a relatively simplified process, and with higher yields than the analogous processes of the prior art as mentioned above, is made possible.

The products which can be obtained by the process of the invention are advantageously used as anaesthetics, or, after suitable dehalogenation or dehydrohalogenation, by known processes, as comonomers in the preparation of fluorinated polymers.

The following Examples are supplied to the purpose of illustrating the invention, and are not to be intended as limitative thereof.

In the Examples, parts and percentages are by weight, unless differently stated.

EXAMPLE 1

To a cylindrical reactor of Algoflon ® having an inner diameter of 85 mm and an useful volume of 1000 ml, kept at a controlled temperature of −75° C., 100 g of 1,2-dichloroethylene (30/70 by weight cis/trans isomeric mixture) and 1000 g of $CCl_3F$ are charged.

The elemental fluorine, diluted to the molar ratio of 1 part with 9 nitrogen parts, is continuously fed over eight hours to the total amount of 1 mol.

At the end of the test, raw reaction product (1130 g) is collected, which is washed with an aqueous solution containing 5% by weight of NaOH, then thoroughly dried over $CaCl_2$, and submitted to distillation to separate the product from the solvent. The conversion into reaction products is of 73% relatively to CHCl=CHCl supplied, and the yield to CHClF=CHClF is of 72% relatively to the reacted matter.

EXAMPLE 2

The test of Example 1 is repeated by feeding an amount of 1.5 mol of $F_2$ over 8 hours.

The conversion is of 80% and the yield is of 74%.

EXAMPLE 3

To the reactor of Example 1, kept at a controlled temperature of −60° C., charged are 100 g of 1,2-dichloro-ethylene (30/70 w/w cis/trans isomeric mixture) and 1000 g of $CCl_3F$.

Elemental fluorine, diluted to the molar ratio of 1 part of $F_2$ to 9 parts of nitrogen, is continuously fed over 8 hours to the total amount of 1 mol fluorine.

At the end of the test, raw reaction product (1110 g) is collected which is purified as described in Example 1. The conversion is of 80% and the yield to CHClF-CHClF is of 63%.

EXAMPLE 4

To the reactor as of Example 1, kept at a controlled temperature of −80° C., 100 g of 1,2-dichloroethylene (isomeric cis/trans ratio=30/70 w/w) and 1000 g of $CCl_3F$ are charged.

Elemental fluorine, diluted to the molar ratio of 1 part of $F_2$ to 9 parts of nitrogen, is continuously fed over 8 hours to the total amount of 1 mol fluorine.

At the end of the test, raw reaction product is collected (1130 g). The conversion is of 68% and the yield to CHClF-CHClF is of 74%.

EXAMPLE 5

To the reactor of Example 1, kept at a controlled temperature of −75° C., 100 g of 1,2-dichloroethylene (100% of cis isomer), and 1000 g of $CCl_3F$ are charged. Elemental fluorine, diluted to the molar ratio of 1 part of $F_2$ to 15 parts of nitrogen, is continuously fed over 8 hours to the total amount of 1 mol fluorine. At the end of the test, 1120 g of raw reaction product are collected. The conversion is of 75% and the yield to CHClF-CHClF is of 70%.

EXAMPLE 6

To the reactor of Example 1, kept at a controlled temperature of −75° C., 100 g of 1,2-dichloroethylene (100% of trans isomer), and 1000 g of $CCl_3F$ are charged.

Elemental fluorine, diluted to the molar ratio of 1 part of $F_2$ to 9 parts of nitrogen, is continuously fed over 8 hours, to the total amount of 1 mol fluorine.

At the end of the test, 1125 g of raw reaction product are collected, with a conversion is of 70% and a yield to CHClF-CHClF of 74%.

EXAMPLE 7

To the reactor as of Example 1, kept at a controlled temperature of −75° C., 100 g of trichloroethylene, and 1000 g of $CCl_3F$ are charged. Elemental fluorine, diluted to the molar ratio of 1 part of $F_2$ to 15 parts of nitrogen is continuously fed over 8 hours, to the total amount of 1 mol fluorine.

At the end of the test, 1135 of raw reaction product are collected, with a conversion of 79% and a yield to $CCl_2F$-CHClF of 93%.

We claim:

1. A process for preparing a hydrofluoroalkane or a hydrohalofluoralkane of the formula:

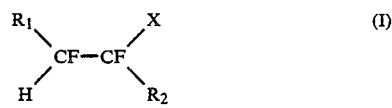
(I)

starting from a hydroalkene or a hydrohaloalkene of the formula:

(II)

and/or

(III)

wherein:

X=H, F, Cl or Br; and $R_1$, $R_2$=H, F, Cl, Br, $C_1$-$C_3$-alkyl or $C_1$-$C_3$-alkoxy in which the H atoms may also be completely substituted by Cl or F, characterized in that hydroalkene or hydrohaloalkene is reacted in the liquid phase with elemental fluorine diluted with an inert gas at a temperature between −70° and −100° C., the molar ratio inert gas/fluorine being between 5 and 15.

2. Process according to claim 1, wherein the temperature is within the range of from −70° C. to −85° C.

3. Process according to claim 1, wherein the liquid reaction phase is constituted by the reactant and by the reaction products, in the form of a mixture with a perhalogenated inert solvent.

4. Process according to claim 3, wherein the amount of solvent used is within the range of from 1 to 20 parts by weight per each part of reactant compound.

* * * * *